United States Patent

Montoro et al.

[11] 3,982,002
[45] Sept. 21, 1976

[54] VINCAMINE 2-KETOGLUTARATE AND COMPOSITIONS CONTAINING VINCAMINE 2-KETOGLUTARATE

[75] Inventors: Fernando Montoro; Antonio Vila-Coro; José Calatayud, all of Madrid, Spain

[73] Assignee: Especialidades Latinas Medicamentos Universales S.A., Madrid, Spain

[22] Filed: Feb. 5, 1975

[21] Appl. No.: 547,191

[30] Foreign Application Priority Data
Sept. 6, 1974 France .............................. 74.30299

[52] U.S. Cl. .......................... 424/267; 260/293.53
[51] Int. Cl.² ........................................ C07D 401/04
[58] Field of Search ................. 260/293.53; 424/267

[56] References Cited
UNITED STATES PATENTS
3,891,640 6/1975 Plat et al. .................... 260/247.5 FP Primary Examiner—G. Thomas Todd
Attorney, Agent, or Firm—Eyre, Mann, Lucas & Just

[57] ABSTRACT

The new compound vincamine 2-ketoglutarate of the formula:

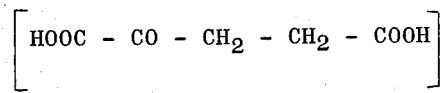

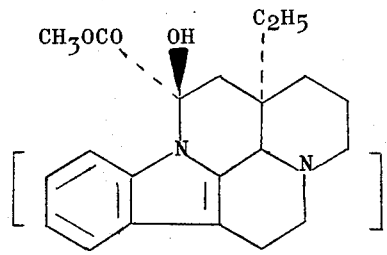

is disclosed and is prepared by mixing 2-ketoglutaric acid and vincamine or a salt thereof in a solvent and recovering the resulting vincamine 2-ketoglutarate which has interesting properties as a vasodilator and brain oxygenator. The vincamine may be prepared by allowing a mixture of a solution of 16-epivincamine and a quaternary ammonium hydroxide to stand whereafter the vincamine is recovered.

3 Claims, 1 Drawing Figure

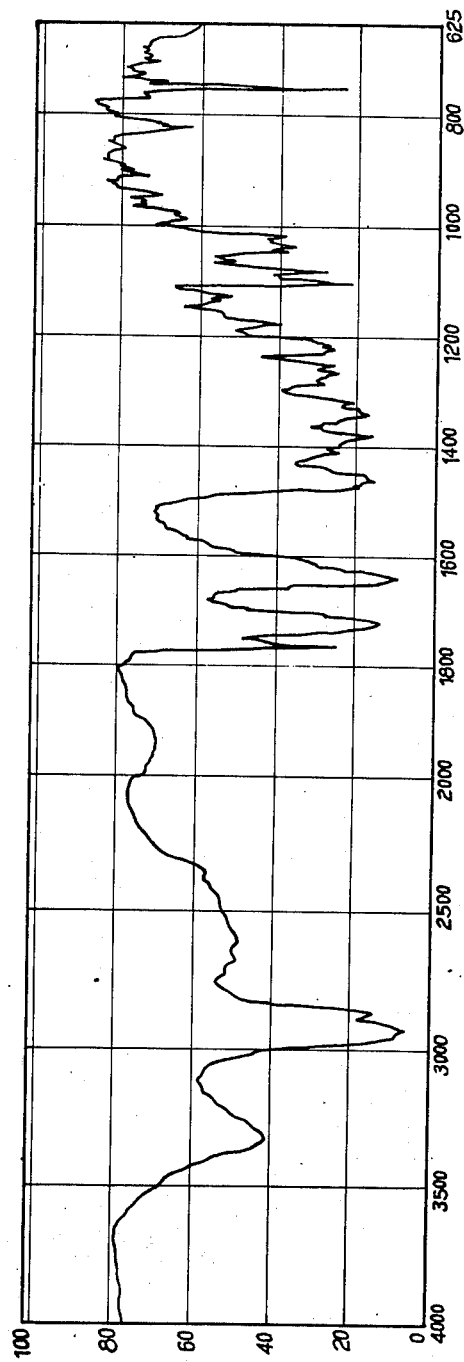

VINCAMINE 2-KETOGLUTARATE AND COMPOSITIONS CONTAINING VINCAMINE 2-KETOGLUTARATE

FIELD OF THE INVENTION

This invention relates to the new compound vincamine 2-ketoglutarate and to compositions containing vincamine 2-ketoglutarate. This invention also relates to a process for the preparation of vincamine 2-ketoglutarate.

Vincamine 2-ketoglutarate is a new vincamine salt which in comparison with other, known salts of vincamine, has advantageous properties, particularly when it is used as the active ingredients in medicinal compositions.

The salt vincamine 2-ketoglutarate has the formula:

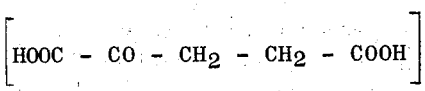

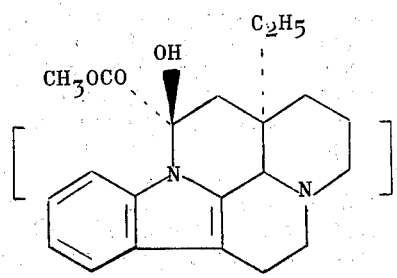

PREPARATION

Vincamine 2-ketoglutarate may be prepared using vincamine or 16-epivincamine as a starting material.

Vincamine 2-ketoglutarate is prepared from vincamine by forming a mixture of 2-ketoglutaric acid and vincamine or on of its known salts in at least one solvent, and recovering the resulting vincamine 2-ketoglutarate. In order to form this mixture, it is preferred to use a slight molar excess of 2-ketoglutaric acid in relation to vincamine. The salt may then be precipitated or recovered by evaporating the solvent from the mixture, by cooling the mixture, or by adding a liquid such as ethyl ether, benzene, toluene, or petroleum ether, which is miscible with the solvent used to form the initial mixture.

Vincamine 2-ketoglutarate is prepared from 16-epivincamine by intimately mixing a solution of 16-epivincamine in a suitable solvent with a compound of the formula:

(I)

in which $R_1$, $R_2$, $R_3$ and $R_4$ are identical or different and each represent an alkyl radical having from 1 to 4 carbon atoms, an aryl radical or an aralkyl radical in which the alkyl part has from 1 to 3 carbon atoms. After allowing the resulting mixture to stand, the vincamine which is formed by isomerisation is extracted by adding water to the mixture, extracting with chloroform, and then separating by chromatography. The resulting vincamine is then reacted with 2-ketoglutaric acid either in the manner described above or in a solvent for the acid, and the vincamine 2-ketoglutarate which is formed by this reaction is precipitated.

Preferably the isomerization of 16-epivincamine is effected using from 0.1 to 0.5 mole per mole of 16-epivincamine of the compound of formula (I).

The solvent in which the 16-epivincamine is dissolved may be an alcohol, such as methanol, propanol or isopropanol; acetonitrile; dimethyl formamide; methyl acetate, or ethyl acetate, etc. The resulting mixture of 16-epivincamine and the compound of formula (I) is allowed to stand at a temperature preferably between ambient temperature, that is to say about 19°C., and a temperature of 40°C. for a time, which may for example vary from 30 minutes to 10 hours.

After the mixture has been allowed to stand, the vincamine which is formed may be extracted, for example, by pouring water into the mixture, and extracting the vincamine with chloroform, whereafter the vincamine is separated by chromatography on silica gel, using as eluant a mixture of ether and ethyl acetate in proportions by volume of about 1:1, the mixture containing increasing amounts of methanol.

Vincamine is thus obtained in a yield which may vary from 10 to 50%, the vincamine being mixed with very small amounts of apovincamine.

The yield of the process of isomerisation of 16-epivincamine with a compound of formula (I) may depend on the temperature and time during which the mixture is allowed to stand after the 16-epivincamine has been brought into contact with the product of formula (I).

The compounds of formula (I) which are suitable for effecting the isomerisation include, for example, benzyltrimethylammonium hydroxide of the formula:

(I)a and tetrabutylammonium hydroxide of the formula:

(I)b

PREFERRED EMBODIMENTS OF THE INVENTION

The following non-limitative Examples illustrate the invention.

Example 1

12 g. (0.082 mole) of 2-ketoglutaric acid are dissolved in 500 ml. of methanol. The solution is brought to the boil and 22.5 g. (0.0635 mole) of vincamine are added a small amount at a time, with vigorous agitation. When dissolution is complete, the resulting solution is concentrated in a rotary evaporator until its volume is reduced to 200 ml. On cooling, 22 g. of vincamine 2-ketoglutarate are obtained. By adding 500 ml. of ethyl ether to the mother liquors, a further amount of 9.6 g. of the salt are obtained. The total amount of salt obtained is therefore, 29.6 g. (yield 93%). The melting point is 214°–215°C.

Elemental analysis for C, H, N and O: Calculated % : C 62.37, H 6.40, N 5.60, O 25.63. Found % : C 62.18, H 6.30, N 5.30, O (by difference) 26.22.

The accompanying drawing shows the infrared spectrum of vincamine 2-ketoglutarate in "Nujol" (Registered Trade Mark) and it can be seen that peaks are obtained at 3420, 2750–2300, 1760, 1720, 1640, 740 cm$^{-1}$. An infrared spectrum was also made in a mixture of "Nujol" and triethylamine, and peaks were obtained at 1750, 1715, 1610–1600 cm$^{-1}$.

The ultraviolet absorption spectrum in methanol gave the following results:

$$\lambda \max 267 \pm 2 \, nm \, E \frac{1\%}{1\,cm} = 173$$

$$220 \pm 2 \, nm \, D \frac{1\%}{1\,cm} = 632$$

Example 2

650 ml. of vincamine hydrochloride (1.66 millimole) are dissolved in 10 ml. of water, and, after vibration, a solution of 248 mg. (1.73 millimole) of 2-ketoglutaric acid and 145 mg. of sodium bicarbonate in 3 ml. of water is added. After being allowed to stand and cool, 453 mg. of vincamine 2-ketoglutarate are obtained. The resulting solution is concentrated in a rotary evaporator to one third of the original volume and, after cooling, an additional amount of 287 mg. of salt are obtained. A total of 740 mg. of salt is thus obtained, that is to say, a yield of 89%.

Example 3

1.617 g. of vincamine (0.005 mole) is dissolved in 15 ml. of chloroform, and 0.8 g. (0.055 mole) of 2-ketoglutaric acid previously dissolved in 5 ml. of methanol is added. After concentration of the resulting solution in a rotary evaporator until a volume of 5 ml. is obtained, 1.75 g. of vincamine 2-ketoglutarate is obtained. By subsequent successive concentrations, an additional amount of 0.5 g. of salt is obtained. A total of 2.25 g. is thus obtained (yield 90%).

Example 4

177 mg. (0.5 millimole) of 16-epivincamine are dissolved in 100 ml. of methanol and 84 mg. (0.2 millimole) of a 40% solution of benzyltrimethylammonium hydroxide of formula (I)a in methanol are added.

The resulting mixture is allowed to stand for 1 hour at a temperature of from 30° to 40°C., and then for 4 hours at ambient temperature (20°C.). The mixture is poured into 30 ml. of water, extracted three times, each with 10 ml. of chloroform, washed with water, and chromatographed on silica gel of from 35 to 70 mesh (ASTM standard), using as eluant a mixture of ether and ethyl acetate in proportions by volume of 1:1, the mixture containing increasing quantities of methanol. 5 mg. of apovincamine, 81 mg. of vincamine (45.5%), and 73 mg. of 16-epivincamine are thus obtained.

The vincamine obtained in this manner is then reacted with 2-ketoglutaric acid by the method described in Example 1.

Example 5

The isomerisation of 16-epivincamine as described in Example 4 is repeated but the time during which the mixture is allowed to stand at ambient temperature is varied. If this time is 10 hours, 38.7 mg. of vincamine are obtained (yield 22%); if this time is 30 minutes, 18 mg. of vincamine are obtained (yield 10.1%).

Example 6

If the isomerisation of 16-epivincamine described in Example 4 is repeated but using 177 mg. (0.5 millimole) of 16-epivincamine in 20 ml. of methanol and 130 mg. (0.2 millimole) of a 40% aqueous solution of tetrabutylammonium hydroxide (formula (I)b), and the mixture is allowed to stand for 5 hours at 25°C. 64 mg. of vincamine are obtained (yield 36%).

MEDICAL PROPERTIES AND USES

Vincamine 2-ketoglutarate is particularly useful as a vasodilator and brain oxygenator medicament and has markedly improved properties in comparison with vincamine and its known salts.

Vincamine 2-ketoglutarate has in fact good solubility in water and very low toxicity and, in comparison with vincamine, gives rise to a greater reduction of cerebral capillary resistance in the presence of a lower reduction of arterial pressure at peripheral level, this reduction being of very short duration. Furthermore, in relation to vincamine, the duration of its cerebral action is longer.

The fact that vincamine 2-ketoglutarate has good solubility in water (8.3%) is a surprising phenomenon having regard to the fact that vincamine and most of its known salts are insoluble in water. This good solubility in water permits easier administration of the vincamine 2-ketoglutarate in injectable form and greater bioavailability of the product in the organism, with improved local tolerance.

Furthermore, the ketoglutaric acid part of the salt has the property of easily passing through the haematoencephalic barrier, causing reduction of intoxication by ammonia at brain level.

Acute toxicology tests show that the vincamine 2-ketoglutarate has very low toxicity, the salt having a $DL_{50}$ of 270 and 300 mg./kg. for the mouse and rat respectively when administered intraperitoneally and a $DL_{50}$ higher than 1 g./kg. when administered orally. The very low toxicity of the salt is particularly advantageous because is maximum vasodilatory activity occurs with a dosage of from 1 to 5 mg./kg. In experimental pharmacological tests, chronic toxicology tests were also carried out by administering the salt at a dosage of 10 mg./kg./day to rats over a period of three months. All that was found was the existence of haemorrhages, which were considered normal in view of the fact that they constitute the epiphenomenon of the vasodilatory properties of the salt. Furthermore, in tetratological studies no malfunction was found in descendants.

The effects of vincamine 2-ketoglutarate on the brain were determined by the conventional methods usually employed. Since the action of vincamine is mainly connected with the appearance of a reduction of capillary and arterial peripheral resistances, comparison of the pharmacological properties of the salt of the invention in relation to vincamine in the form of its known salts was made principally by studying this parameter.

In order to measure the torcular effect, the products were administered intravenously to a rabbit anaesthetised with urethane, and the arterial pressure was measured with the aid of a mercury pressure gauge connected to the common carotid artery. The doses used for vincamine and for vincamine 2-ketoglutarate are 0.4, 0.8 and 2.0 mg./kg. (expressed as vincamine base). Acetycholine, theophylline, and papaverine were also used as controls. As can be seen in Table 1 below, vincamine 2-ketoglutarate gives rise to a lowering of arterial pressure of very short duration, this duration being much shorter than that resulting from the administration of vincamine or its known salts.

Tests relating to cerebral circulation showed that vincamine 2-ketoglutarate gives rise to a reduction of cerebral vascular resistance which is maximum with doses amounting to one fifth of these necessary to obtain the same effect with the aid of vincamine. As can be seen in Table II below, this action has a duration which in the case of vincamine 2-ketoglutarate is more than twice that obtained with vincamine in this experiment; the method used was adapted from that described in "Pharmacological experiments in intact preparations" (Ed. Livingstone, 1970) by isolating the cerebral blood circuit of the rabbit, anaesthetised with urethane, by bilateral ligature of the outer carotid arteries, the brain being connected to the carotidian circuit by ligature of the vertebral arteries situated between the cervical vertebrae III and IV. The brain was perfused carotidally by means of a peristaltic bomb, connecting a pressure transducer to measure vascular resistance indirectly. Arterial pressure is measured simultaneously with the aid of a mercury pressure gauge. The products were administered intravenously through the jugular vein. The results indicate that vincamine 2-ketoglutarate has obvious tropism in relation to the central nervous system. Taking into account its greater activity and the longer duration of its action, vincamine 2-ketoglutarate gives rise to better cerebral oxygenation. Used as a medicament, vincamine 2-ketoglutarate makes it possible to treat cerebral vascular accidents, states of cerebral anoxemia or preanoxemia, cerebral sclerosis, hemiplegia and hemiparesis, and post-traumatic comas, with doses which can be administered orally or parenterally and which may be close to 100 mg. a day, having regard to the very low toxicity of the salt. Obviously, in view of the activity of vincamine 2-ketoglutarate, it is also possible to obtain therepeutical effects with a dosage of 10 mg./day or less. The doses indicated above are obviously given only by way of example and may obviously be modified, particularly taking into account the gravity of the illness treated.

TABLE I

|  | Dose μg./kg. | Duration of effect in minutes | Reduction of pressure, mm. Hg |
|---|---|---|---|
| Vincamine | 400 | 4.5 | 4 |
|  | 800 | 5.2 | 6 |
|  | 2,000 | 8.1 | 10 |
| Vincamine 2-ketoglutarate | 400 | 1.5 | 12 |
|  | 800 | 1.5 | 16 |
|  | 2,000 | 1.5 | 18 |

TABLE II

|  | Dose μg./kg. | Duration of effect in minutes | Reduction of peripheral resistance mm. Hg |
|---|---|---|---|
| Vincamine | 400 | 10 | 1.5 |
|  | 800 | 10 | 2 |
|  | 2,000 | 15 | 5 |
| Vincamine 2-ketoglutarate | 400 | 25 | 4 |
|  | 800 | 30 | 6 |
|  | 2,000 | 30 | 5 |

What is claimed is:

1. Vincamine 2-ketoglutarate of the following formula:

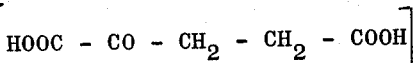

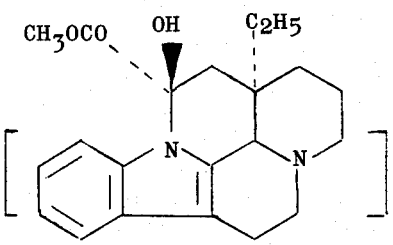

2. Process for the treatment of cerebral vascular accidents, states of cerebral anoxemia or preanoxemia, cerebral sclerosis, hemiplegia and hemiparesis, and post-traumatic comas comprising the oral or parenteral administration of a therapeutically effective amount of a product of the formula:

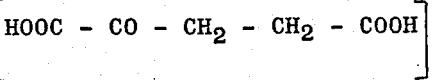

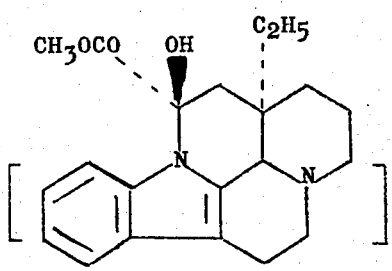

3. Process according to claim 2 wherein said product is administered at the rate of from about 10 to about 100 mg/day.

* * * * *